ately, which up to now bendazac could only be used topically.

United States Patent [19]
Silvestrini et al.

[11] 4,352,813
[45] Oct. 5, 1982

[54] [(1-BENZYL-1H-INDAZOL-3-YL)OXY] ACETIC ACID SALT WITH L. LYSINE

[75] Inventors: Bruno Silvestrini; Leandro Baiocchi, both of Rome, Italy

[73] Assignee: Aziende Chimiche Riunite Angelini Francesco A.C.R.A.F. S.p.A., Rome, Italy

[21] Appl. No.: 269,923

[22] Filed: Jun. 2, 1981

[30] Foreign Application Priority Data

Jul. 29, 1980 [IT] Italy ............................... 23768 A/80

[51] Int. Cl.³ .................. A61K 31/415; C07D 231/56
[52] U.S. Cl. ................................. 424/273 N; 548/372
[58] Field of Search .................... 548/372; 424/273 N

[56] References Cited

U.S. PATENT DOCUMENTS

3,470,194  9/1969  Palazzo ............................... 548/372

FOREIGN PATENT DOCUMENTS

1530097  6/1968  France .

OTHER PUBLICATIONS

Yabuuchi et al., Chem. Abst. 1975, vol. 82, No. 156290y.
Allori et al., Clinica Europea, 1975, vol. XIV, No. 6, pp. 1–11.

*Primary Examiner*—Henry R. Jiles
*Assistant Examiner*—N. Harkaway
*Attorney, Agent, or Firm*—Ladas & Parry

[57] ABSTRACT

A new salt of [(1-benzyl-1H-indazol-3-yl)oxy] acetic acid (or bendazac) with L. lysine.

Following oral administrations of this compound in man, the concentrations of bendazac found in the blood are higher than those obtained after administration of bendazac as such.

This discovery extends the therapeutic use of bendazac. In fact, whereas up to now bendazac could only be used topically, the L. lysine salt of bendazac makes it possible to perform therapeutic treatments with the oral route of administration as an agent with a normalizing effect on blood lipids.

3 Claims, No Drawings

[(1-BENZYL-1H-INDAZOL-3-YL)OXY] ACETIC ACID SALT WITH L. LYSINE

In the following: Italian Pat. No. 1,043,762 granted on Feb. 29, 1980 and entitled "Acidi [(1H-indazol-3-il) ossi] acetici e processo per la loro preparazione", corresponding to U.S. Pat. No. 3,470,194 granted on Sept. 30, 1969 and Italian Patent Application No. 15267, filed on Apr. 21, 1967, also pending and entitled "Acidi "(1H-indazol-3-il)ossi] alcanoici e processo per la loro preparazione" it is claimed a series of compounds belonging to the general formula

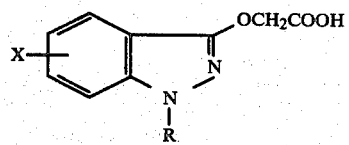

and possessing interesting pharmacological properties. Particularly [(1-benzyl-1H-indazol-3-yl)oxy] acetic acid (bendazac) was found to be very interesting as a local antiinflammatory agent and it was introduced in medicine and used for this activity.

The [(1H-indazol-3-yl)oxy] alkanoic acids particularly [(1-benzyl-1H-indazol-3-yl)oxy] acetic acid, are only slightly absorbed, even as a salt with alkaline, alkaline-earth metals or with organic bases such as morpholine, diethanolamine, piperazine, triethanolamine, diisopropylamine, hydroxyethylmorpholine. The bendazac blood concentrations are found in any case to be too low to permit the systemic use of the drug.

As reported by Silvestrini, Catanese and Lisciani in "Proceedings of an International symposium on inflammation Biochemistry and Drug Interaction" Excerpta Medica International Congress Series No. 188 (1968)—the mean serum concentration found in man after an 8-day treatment with daily doses from 150 to 900 mg is only 8 μg/ml.

It has now been found that [(1-benzyl-1H-indazol-3-yl)-oxy] acetic acid (bendazac) as a salt with L. lysine has a better absorption. As shown in Table I, after a single oral administration of 500 mg of L. lysine salt, corresponding to about 300 mg of [(1-benzyl-1H-indazol-3-yl)-oxy] acetic acid, the mean serum concentration found in 6 volunteers, two hours after administration, is 30 μg/ml; under the same conditions, the blood concentration obtained with 300 mg [(1-benzyl-1H-indazol-3-yl)-oxy] acetic acid or bendazac is 8 μg/ml.

The availability of a bendazac salt (L. lysine salt) capable of producing higher blood concentrations than those previously obtained with bendazac gave results which modify the drug's possible uses.

TABLE I

Serum concentrations in man after a single oral administration of bendazac as such or bendazac salt with L. lysine.

| Compound | Sex | Weight in kg | Dose in mg | Concentrations in μg/ml | | | |
|---|---|---|---|---|---|---|---|
| | | | | 1 hr | 2 hr | 4 hr | 8 hr |
| bendazac | ♂ | 50 | 300 | 6 | 15 | 12 | 8 |
| | | 70 | | 7 | 10 | 8 | 5 |
| | | 80 | | 2 | 9 | 7 | 4 |
| | ♀ | 60 | | 5 | 16 | 6 | 4 |
| | | 50 | | 8 | 9 | 9 | 5 |
| | | 40 | | 3 | 11 | 10 | 4 |
| X̄ ± SE | | | | 5.2 ± 0.94 | 11.7 ± 1.26 | 8.7 ± 0.88 | 5.0 ± 0.63 |
| bendazac salt with L. lysine | ♂ | 60 | 500 (equiv. to about 300 of acid) | 15 | 56 | 25 | 10 |
| | | 55 | | 20 | 32 | 16 | 8 |
| | | 80 | | 18 | 37 | 18 | 9 |
| | ♀ | 75 | | 23 | 46 | 30 | 16 |
| | | 60 | | 20 | 27 | 10 | 5 |
| | | 45 | | 15 | 22 | 11 | 5 |
| X̄ ± SE | | | | 18.5 ± 1.28 | 36.7 ± 5.13 | 18.3 ± 3.21 | 8.8 ± 1.66 |

In man, a study was conducted on 8 patients with dyslipemia. The patients were treated with 658 mg of bendazac salt with L. lysine (corresponding to 400 mg of bendazac) in capsule form three times a day.

The results obtained are summarized in Table II.

TABLE II

Effects of bendazac salt with L. lysine on blood levels* of total lipids, cholesterol and triglycerides
Study on 8 patients

| | Duration of treatment in weeks | | |
|---|---|---|---|
| | 0 | 1 | 3 |
| Total lipids | 1100 ± 194 | 1147 ± 138 | 1186 ± 118 |
| Cholesterol | 219 ± 38 | 205 ± 29 | 165 ± 18 |
| Triglycerides | 181 ± 50 | 140 ± 26 | 122 ± 27 |

*in mg %

It should be pointed out that the results of the above study were published (Allori and Silvestrini, 1975), without mentioning, however, that bendazac was used as a salt with L. lysine. Since this fact was known only by the Autors of the present invention it follows that the discovery of the properties of the salt of bendazac with L. lysine has not been disclosed till now.

After 3 weeks of treatment, there was a marked decrease of the amount of cholesterol in the blood. A reduction of triglycerides, already evident after a week, was also noted. The intensity of its normalizing effect on blood lipids is such to justify the therapeutic use of bendazac salt with L. lysine.

In evaluating the significance of the above results, the following should be taken into consideration:

(a) the obtaining of sufficiently high blood levels with bendazac salt with L. lysine to permit the systemic use of the drug has not been previously described in literature;

(b) the possible systemic use of bendazac salt with L. lysine constitutes a novelty as compared to the previous uses of this substance.

In order to obtain the bendazac salt with L. lysine the preparation is performed by heating, preferably in ethanol or water-acetone, equimolecular quantities of [(1-benzyl-1H-indazol-3-yl)oxy] acetic acid and the aminoacid. The salt crystallizes on cooling as a bihydrate.

The so-obtained salt can be used as such or after drying under vacuum to constant weight. Both the bihydrate and the anhydrous salts with one of two optically active forms of lysine, as well, as the salt with racemic lysine are employed in different pharmaceutical forms.

In use, the compound of the invention is administered orally in conventional formulations, namely in association with pharmaceutical excipients generally used for the production of compositions for oral administration. Single doses between 0.250 g and 1 g have to be administered 2–3 times a day.

Conventional pharmaceutical compositions for oral administration may be used such as tablets and capsules; the unit dose for both tablet and capsule of active ingredient may be 250 mg.

The carriers used in the preparation of these compositions are the excipients known in the pharmacist art. In the preparation of tablets, typical excipients include disintegrating agents, e.g. maize starch and lubricant agents, e.g. magnesium stearate; in the preparation of capsules, standard gelatin capsules may be used containing the active ingredient alone or admixed with a diluent.

The following non-restrictive examples illustrate the preparation of the salt which is the matter of the present invention.

EXAMPLE 1

Salt of [(1-benzyl-1H-indazol-3-yl)oxy] acetic acid with L. lysine.

12 g (0.042 mol) of [(1-benzyl-1H-indazol-3-yl) oxy] acetic acid and 6.2 g (0.042 mol) of L. lysine were dissolved in 100 ml of 95% ethanol by heating. The mixture was filtered warm in order to remove the very small amounts of impurities and it was then left to stand overnight at room temperature. The crystalline product was filtered and recrystallized from 95% ethanol: 15 g of the salt were first obtained (yield 75,9%) while the mother-liquor yielded more product. The compound consists of one molecule of [(1-benzyl-1H-indazol-3-yl)oxy] acetic acid, one of L. lysine and two of crystallization-water; the same shows melting point 178°–81° C. with loss of water during heating.

EXAMPLE 2

The salt obtained according to the Example 1 was dried under vacuum (5–10 Torr.) at 105° C. to constant weight: in such a form it shows melting point 178°–81° with decomposition.

What we claim is:

1. A salt of [(1-benzyl-1H-indazol-3-yl)oxy] acetic acid with L. lysine.

2. A pharmaceutical composition for use in the treatment of high blood lipids levels comprising an amount of the compound of claim 1 effective in said treatment together with a pharmaceutically acceptable carrier.

3. A method for the treatment of humans suffering from high blood lipid levels comprising orally administering to said human being an amount of the compound of claim 1 effective to decrease high blood lipid levels.

* * * * *